United States Patent [19]

Carson

[11] 3,950,355

[45] Apr. 13, 1976

[54] 5-CHLOROCARBONYL-PYRROLES

[75] Inventor: John Robert Carson, Norristown, Pa.

[73] Assignee: McNeil Laboratories, Inc., Fort Washington, Pa.

[22] Filed: Apr. 18, 1974

[21] Appl. No.: 491,076

Related U.S. Application Data

[62] Division of Ser. No. 277,845, Aug. 3, 1972, Pat. No. 3,846,447.

[52] U.S. Cl. ............................................ 260/326.2
[51] Int. Cl.² ..................................... C07D 207/24
[58] Field of Search ................................ 260/326.2

[56] References Cited

FOREIGN PATENTS OR APPLICATIONS 395,092   4/1924   Germany ......................... 260/326.2

OTHER PUBLICATIONS

Chem. Abstr., Vol. 72, (1970), 12557m, 12558n.

Primary Examiner—Frederick E. Waddell
Attorney, Agent, or Firm—Salvatore R. Conte

[57] ABSTRACT

A process of preparing certain 5-aroyl-pyrrole-2-alkanoic acid derivatives using phosgene and certain 5-unsubstituted pyrroles as starting materials, and certain novel 5-chlorocarbonyl-pyrrole precursors.

5 Claims, No Drawings

5-CHLOROCARBONYL-PYRROLES

This is a divisional application of my co-pending application Ser. No. 277,845, filed Aug. 3, 1972, now U.S. Pat. No. 3,846,447.

BACKGROUND OF THE INVENTION

5-Aroyl-pyrroles have been made heretofore by Friedel-Crafts acylation procedures (see Belgian Pat. No. 762,060). The subject process reacts phosgene with appropriate 5-unsubstituted pyrroles and the thus-obtained 5-chlorocarbonyl-pyrroles are then transformed into the desired 5-aroyl-pyrroles.

DESCRIPTION OF THE PREFERRED EMBODIMENTS

This invention relates to a novel method of preparing 5-aroyl-pyrrole-2-alkanoic acid derivatives of the formula:

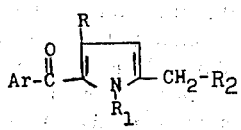

(1)

wherein R represents a member selected from the group consisting of hydrogen and lower alkyl, preferably methyl;

$R_1$ represents lower alkyl, preferably methyl;

$R_2$ represents a member selected from the group consisting of CN, COO(lower alkyl) and COOH; and Ar represents a member selected from the group consisting of phenyl and phenyl substituted with one or more members selected from the group consisting of halo, lower alkyl, lower alkoxy, trifluoromethyl and methylthio;

provided that, when said R is lower alkyl, then said $R_2$ is other than CN.

As used herein, "lower alkyl" and "lower alkoxy" may be straight or branch chained and have from 1 to about 6 carbon atoms, such as, for example, methyl, ethyl, propyl, isopropyl, butyl, pentyl, hexyl and the like alkyls, and, respectively, the corresponding alkoxys such as, for example, methoxy, ethoxy, propoxy, isopropoxy, etc.; and the term "halo" stands for chloro, bromo, fluoro and iodo. Among the prefered substituted phenyls embraced by the symbol "Ar" are mono-, di-and tri-substituted phenyls, particularly the mono- and di-substituted phenyls, wherein each substituent is a member selected from the group consisting of halo, lower alkyl, lower alkoxy, trifluoromethyl and methylthio.

The compounds of formula (I) possess anti-inflammatory activity (see Belgian Patent No. 762,060). The following novel and advantageous process may be used to prepare said compounds. The symbol "Z" denotes the nitrile and ester forms of (I), that is, Z represents a member selected from the group consisting of CN and COO(lower alkyl).

According to the instant process, phosgene (II) is reacted with an appropriate 5-unsubstituted pyrrole of formula (III) in a suitable inert aprotic solvent such as, for example, an aromatic hydrocarbon, e.g., benzene, toluene, xylene and the like; an ether, e.g., diethyl ether, tetrahydrofuran, dioxane and the like; and a halogenated lower alkane, e.g., chloroform, methylene chloride, 1,2-dichloroethane and the like. If desired, an appropriate halogen acid acceptor, e.g., an amine base such as triethylamine, may be employed as a scavenger to pick up the HCl that is eliminated during the course of the reaction. Temperatures ranging from about 0°C. to about 50°C. are generally employed. Although stoichiometric quantities of the two reactants may suitably be employed, a slight molar excess (about 10%) of phosgene is preferred.

The thus-obtained 5-chlorocarbonyl-pyrrole of formula (IV) is then treated with either:

i. an appropriate aryl magnesium halide (Grignard reagent), e.g., a compound of the formula: ArMgBr, wherein Ar is as previously described, in the presence of a catalytic amount of a transition metal halide, such as, for example $ZnCl_2$, $CdCl_2$, $FeCl_3$, $CoCl_3$, $(CuBr)_2$ and the like, at low temperatures, preferably below −50°C.; or ii. an appropriate aryl transition metal compound of the formula: $(Ar)_nM$, wherein Ar is as previously described, M is a transition metal selected from the group consisting of copper, zinc and cadmium, and n is an integer equal to the valence of the particular transition metal salt employed, ambient temperatures generally being employed;

in a suitable aprotic solvent preferably an aromatic hydrocarbon or ether mentioned previously, in order to prepare the desired 5-aroyl-pyrrole nitriles and esters of formula (V). The $(Ar)_nM$ compounds are conveniently prepared in situ by adding a transition metal halide, e.g., cadmium chloride, zinc chloride and the like, to a solution of an appropriate aryl magnesium halide Grignard reagent.

Standard nitrile-to-acid and ester-to-acid hydrolysis procedures are then employed in order to transform the respective nitrile and ester functions to the corresponding acid form of formula (I). The foregoing reactions may be schematically illustrated as follows:

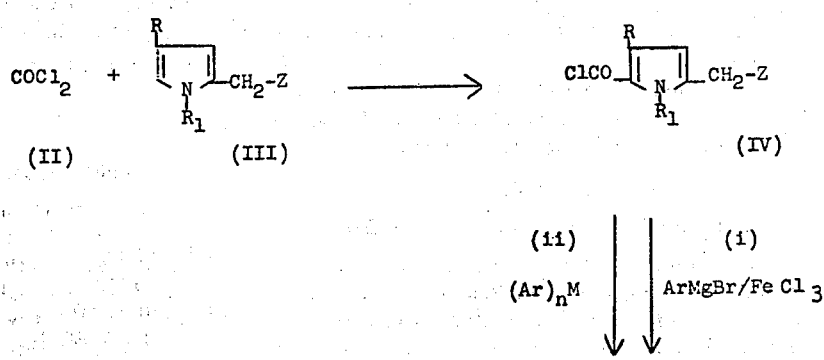

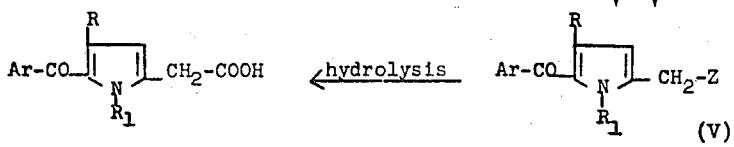

The 5-chlorocarbonyl-pyrroles of formula (IV) are novel compounds and, in view of their utility as intermediates in the synthesis of formula (I) compounds, they constitute an additional feature of this invention as does the method of making same.

The following examples are intended to illustrate, but not to limit, the scope of the present invention. Unless otherwise stated, all parts are by weight.

EXAMPLE I

5-Chlorocarbonyl-1-methylpyrrole-2-acetonitrile

A solution of 6.0 g. (0.05 mole) of 1-methylpyrrole-2-acetonitrile in 50 ml. of ether is added to a solution of 5.85 g. (0.06 mole) of phosgene in 100 ml. of ether. The solution is allowed to stand at room temperature for 18 hours. The solvent is evaporated in vacuo and the residue is recrystallized from ether to give 5.1 g. of 5-chlorocarbonyl-1-methylpyrrole-2-acetonitrile as a red solid, m.p. 78°–80°C.

EXAMPLE II

Ethyl 5-chlorocarbonyl-1-methylpyrrole-2-acetate

A solution of 5.0 g. (0.03 mole) of ethyl 1-methylpyrrole-2-acetate in 20 ml. of ether is added to a solution of 3.34 g. (0.033 mole) of phosgene in 50 ml. of ether at room temperature. After 18 hours the solution is evaporated to dryness in vacuo. The residue is recrystallized from hexane to give 5.9 g. of pink crystalline ethyl 5-chlorocarbonyl-1-methylpyrrole-2-acetate, m.p. 52°–54°C.

EXAMPLE III

Ethyl 5-chlorocarbonyl-1,4-dimethylpyrrole-2-acetate

A solution of 5.0 g. (0.0275 mole) of ethyl 1,4-dimethylpyrrole-2-acetate in 30 ml. of dry ether is cooled to 5° and a solution of 3.2 g. (0.0325 mole) of phosgene in 50 ml. of ether is added dropwise. The mixture is allowed to stand for 16 hours. The solvent is evaporated in vacuo to give 6.7 g. of white crystalline ethyl 5-chlorocarbonyl-1,4-dimethylpyrrole-2-acetate. After the latter is recrystallized from hexane the m.p. is found to be 65°–66°C.

EXAMPLE IV

The procedure of Example II is repeated except that an equivalent quantity of methyl 1-methylpyrrole-2-acetate is used in place of the ethyl ester and used therein to yield, as the respective product, methyl 5-chlorocarbonyl-1-methylpyrrole-2-acetate.

EXAMPLE V

Ethyl 1-methyl-5-(p-toluoyl)-pyrrole-2-acetate

To a solution of 0.0516 mole of p-tolyl magnesium bromide in ether (40 ml.) is added 5.0 g. (0.0274 mole) of cadmium chloride. The mixture is refluxed for 20 minutes, 50 ml. of dry benzene is added and the ether is distilled off. To this solution of di-(p-tolyl) cadmium is added dropwise 5.9 g. (0.0258 mole) of ethyl 5-chlorocarbonyl-1-methylpyrrole-2-acetate in 25 ml. of benzene. The mixture is stirred at room temperature for 1 hour and poured into dilute HCl. The mixture is extracted with ether. The ether extract is washed successively with dimethylaminopropylamine solution, dilute HCl and brine and then dried (anhydrous MgSO$_4$). The solvent is evaporated in vacuo. The residue is crystallized from methyl cyclohexane and recrystallized from ethanol to give white crystalline ethyl 1-methyl-5-p-toluoylpyrrole-2-acetate, m.p. 70°–71°C.

EXAMPLE VI

By repeating the procedure of Example V, except that an equivalent amount of methyl 5-chlorocarbonyl-1-methylpyrrole-2-acetate is substituted for the ethyl ester used therein, there is obtained as the final product: methyl 1-methyl-5-(p-toluoyl)-pyrrole-2-acetate.

EXAMPLE VII

Ethyl 1-methyl-5-(p-toluoyl)-pyrrole-2-acetate

To a stirred and chilled (−60°C.) solution of 5.0 g. (0.022 mole) of ethyl 5-chlorocarbonyl-1-methylpyrrole-2-acetate in 300 ml. of dry toluene is added in one portion 0.70 g. (0.0044 mole) of anhydrous FeCl$_3$, weighed under 5 ml. of toluene and dissolved in 2 ml. of ether. The freshly prepared Grignard solution of 0.023 mole of p-tolylmagnesium bromide in 15 ml. ether is added dropwise, under hydrogen, to the above reaction mixture at such a rate so as to maintain the reaction temperature at −60 ± 2°C. The mixture is stirred at that temperature for another hour, then hydrolyzed with ice water and made strongly acidic with 3N HCl-ice. The aqueous layer is washed 3 times with benzene and the combined organic layers are washed sequentially with 3-dimethylaminopropylamine-ice, 3N HCl-ice, and saturated NaHCO$_3$ solution. The organic layer is dried over anhydrous MgSO$_4$, filtered and the solvent evaporated off to give about 2.0 g. (20%) of a solid residue with thin layer chromatography (film, silica, 1:3 EtOAo/cyclohexane) showing two major spots (rf - 0.54, 0.90). Column chromatography on 50 g. of CC-4 silica and sequential elution with hexane, hexane-benzene, benzene and benzene-ether gives the desired product (eluted with 10% Et$_2$O/benzene) as an oil (0.75 g., 12% yield). Crystallization from MeOH gives about 350 mg. of a white solid, ethyl 1-methyl-5-(p-toluoyl)pyrrole-2-acetate, m.p. 68°–70°C.

EXAMPLE VIII

A. Ethyl 5-(p-chlorobenzoyl)-1,4-dimethylpyrrole-2-acetate

To a freshly prepared Grignard solution of 0.055 mole of p-chlorophenyl magnesium bromide in 50 ml. of anhydrous ether is added 5.5 g. (0.030 mole) of cadmium chloride. The mixture is refluxed for 20 minutes, 50 ml. of benzene is added and the ether is distilled off. To this solution of di-(p-chlorophenyl) cadmium reagent is added dropwise a solution of 6.7 g. (0.0275 mole) of ethyl-5-chlorocarbonyl-1,4-dimethylpyrrole-2-acetate in 50 ml. of benzene. The reaction mixture is stirred at room temperature for another hour and then poured into 3N HCl-ice. The aqueous layer is extracted 4 times with ether and the combined organic layers are washed sequentially with 3-dimethylaminopropylamine-ice, 3N HCl-ice and saturated NaHCO₃ solution. The organics are dried over anhydrous MgSO₄, filtered and then evaporated to give about 7.4 g. of solid residue. Two recrystallizations from MeOH gives about 1.8 g. of the product, ethyl 5-(p-chlorobenzoyl)-1,4-dimethylpyrrole-2-acetate, m.p. 101°–104°C.

B. Ethyl 5-(p-chlorobenzoyl)-1-methylpyrrole-2-acetate

The procedure of Example VIII-A is repeated, except that an equivalent amount of ethyl 5-chlorocarbonyl-1-methylpyrrole-2-acetate is used as the starting material, to yield as the final product: ethyl 5-(p-chlorobenzoyl)-1-methylpyrrole-2-acetate.

EXAMPLE IX

The procedure of Example VIII-A is repeated except that an equivalent amount of methyl 5-chlorocarbonyl-1-methylpyrrole-2-acetate is used in place of the ethyl ester used therein to yield, as the respective product, methyl 5-(p-chlorobenzoyl)-1-methylpyrrole-2-acetate.

EXAMPLE X 5-p-Toluoyl-1-methylpyrrole-2-acetonitrile

To a freshly prepared Grignard solution of 0.0516 mold of p-tolyl magnesium bromide in 40 ml. of ether is added 5.0 g. (0.0274 mole) of cadmium chloride. The mixture is refluxed for 20 minutes, 50 ml. of dry benzene is added and the ether is distilled off. To this solution of di-(p-tolyl) cadmium reagent is added dropwise a solution of 4.67 g. (0.0258 mole) of 5-chlorocarbonyl-1-methylpyrrole-2-acetonitrile in 25 ml. of benzene. The reaction mixture is stirred at room temperature for another hour and then poured into 3N HCl-ice. The aqueous layer is extracted four times with ether and the combined organic layers are washed sequentially with 3-dimethylaminopropylamine-ice, 3N HCl-ice and saturated NaHCO₃ solution. The organics are dried over anhydrous MgSO₄, filtered and then evaporated to give about 3.0 g. (42% yield) of an oily residue containing 5-p-toluoyl-1-methylpyrrole-2-acetonitrile, which is isolated by standard column chromatographic techniques.

EXAMPLE XI

The procedures of Examples V and VII may be followed to prepare the 5-aroyl esters of formula (I) by appropriate choice of starting materials. For example, by repeating said Examples, except that an equivalent quantity of each of the following known aryl magnesium halides is used as the starting Grignard reagent in place of the p-tolyl magnesium bromide used therein:
phenyl-MgBr,
4-bromophenyl-MgBr,
3,4-dimethoxyphenyl-MgBr,
4-trifluoromethylphenyl-MgBr,
4-methylthiophenyl-MgBr,
3,4-dichlorophenyl-MgCl,
3,5-dimethoxyphenyl-MgCl,
3,4-dimethylphenyl-MgBr, and
4-ethoxyphenyl-MgBr
the following respective products are obtained:
ethyl 1-methyl-4-phenylpyrrole-2-acetate,
ethyl 1-methyl-5-(p-bromophenyl)-pyrrole-2-acetate,
ethyl 1-methyl-5-(3',4'-dimethoxyphenyl)-pyrrole-2-acetate,
ethyl 1-methyl-5-(p-trifluoromethylphenyl)-pyrrole-2-acetate,
ethyl 1-methyl-5-(p-methylthiophenyl)-pyrrole-2-acetate,
ethyl 1-methyl-5-(3',4'-dichlorophenyl)-pyrrole-2-acetate,
ethyl 1-methyl-5-(3',5'-dimethoxyphenyl)-pyrrole-2-acetate,
ethyl 1-methyl-5-(3',4'-dimethylphenyl)-pyrrole-2-acetate, and
ethyl 1-methyl-5-(p-ethoxyphenyl)-pyrrole-2-acetate

EXAMPLE XII

The procedure of Example X may be followed to prepare the 5-aroyl nitriles of formula (I) by appropriate choice of starting materials. For example, by repeating Example X, except that an equivalent quantity of each of the aryl magnesium bromides found in Example XI is substituted for the p-tolyl magnesium bromide used therein, there are obtained, as respective products, the corresponding 5-aroyl-1-methylpyrrole-2-acetonitriles of formula (I).

EXAMPLE XIII

A. 5-p-Toluoyl-1-methylpyrrole-2-acetic acid

A solution of 0.02 mole 5-p-toluoyl-1-methylpyrrole-2-acetonitrile in 44 ml. 1N sodium hydroxide and 40 ml. 95% ethanol is heated to reflux for 18 hours. The ethanol is then evaporated in vacuo and the remaining solution poured onto ice acidified with dilute HCl. The resulting precipitate is separated by filtration and recrystallized from ether-hexane. The solid is then partitioned between ether and a saturated solution of NaHCO₃. The NaHCO₃ fraction is separated and acidified with dilute HCl. The precipitate, 5-p-toluoyl-1-methylpyrrole-2-acetic acid, is separated by filtration and purified by recrystallization from ether-methyl cyclohexane solution and dried.

B. By following the nitrile-to-acid hydrolysis procedure of Example XIII-A, except that an equivalent quantity of each nitrile obtained from Example XII is employed as the starting material, the corresponding respective 5-aroyl-pyrrole-2-acetic acids of formula (I) are obtained.

EXAMPLE XIV

A. 5-(p-Chlorobenzoyl)-1,4-dimethyopyrrole-2-acetic acid

A solution of 0.01 mole of ethyl 5-(p-chlorobenzoyl)-1,4-dimethylpyrrole-2-acetate in 12 ml. (0.012 mole) of 1N sodium hydroxide solution and 5 ml. of 95% ethanol is refluxed for 30 minutes. The solution is diluted with water and the ethanol evaporated in vacuo. The remaining solution is filtered and the filtrate acidified with dilute HCl. The precipitated solid is collected by filtration and recrystallized from methanol-water to yield the product, 5-(p-chlorobenzoyl)-1,4-dimethylpyrrole-2-acetic acid.

B. By following the ester-to-acid hydrolysis procedure of Example XIV-A, except that an equivalent quantity of each ester obtained from Examples V, VI, VII and XI is employed as the starting material, the corresponding respective 5-aroyl-pyrrole-2-acetic acids of formula (I) are obtained.

EXAMPLE XV 5-(p-Chlorobenzoyl)-1-methylpyrrole-2-acetic acid

A solution of 3.06 g. (0.01 mole) of ethyl 5-(p-chlorobenzoyl)-1-methylpyrrole-2-acetate in 25 ml. of 0.5 N sodium hydroxide is refluxed for 30 minutes. The solution is cooled, washed with ether and then acidified with dilute HCl. The resulting solid precipitate is collected by filtration, dried and recrystallized from ethanol-water to give the product: 5-(p-chlorobenzoyl)-1-methylpyrrole-2-acetic acid, m.p. 189°–191°C. Upon recrystallization from ethanol-water, the melting point is 188°–190°C.

I claim:

1. A 5-chlorocarbonyl-pyrrole having the formula:

ClCO—[pyrrole with R at 3-position, $R_1$ on N]—$CH_2$—Z wherein
R is a member selected from the group consisting of hydrogen and lower alkyl;
$R_1$ is lower alkyl; and
Z is a member selected from the group consisting of CN and COO(lower alkyl);
provided that, when said R is lower alkyl, then said Z is COO(lower alkyl).

2. 5-Chlorocarbonyl-1-methylpyrrole-2-acetonitrile.

3. Ethyl 5-chlorocarbonyl-1-methylpyrrole-2-acetate.

4. Ethyl 5-chlorocarbonyl-1,4-dimethylpyrrole-2-acetate.

5. Methyl 5-chlorocarbonyl-1-methylpyrrole-2-acetate.

* * * * *

UNITED STATES PATENT AND TRADEMARK OFFICE
CERTIFICATE OF CORRECTION

PATENT NO. : 3,950,355
DATED : April 13, 1976
INVENTOR(S) : Carson, John Robert

It is certified that error appears in the above-identified patent and that said Letters Patent are hereby corrected as shown below:

In Column 4, line 51, the word "EtOAo" should read --- EtOAc ---.

In Column 5, line 35, the word "mold" should read --- mole ---.

In Column 6, line 56, the word "1,4-dimethyopyrrole" should read --- 1,4-dimethylpyrrole ---.

Signed and Sealed this

Twenty-eighth Day of June 1977

[SEAL]

Attest:

RUTH C. MASON
Attesting Officer

C. MARSHALL DANN
Commissioner of Patents and Trademarks